(12) United States Patent
Li (10) Patent No.: US 7,184,138 B1
(45) Date of Patent: Feb. 27, 2007

(54) SPATIAL FILTER FOR SAMPLE INSPECTION SYSTEM

(75) Inventor: Bo Li, Palo Alto, CA (US)

(73) Assignee: KLA Tencor Technologies Corporation, Milpitas, CA (US)

( * ) Notice: Subject to any disclaimer, the term of this patent is extended or adjusted under 35 U.S.C. 154(b) by 443 days.

(21) Appl. No.: 10/798,024

(22) Filed: Mar. 11, 2004

(51) Int. Cl.
*G01N 21/00* (2006.01)
*G01B 11/30* (2006.01)

(52) U.S. Cl. .............................. 356/237.2; 356/239.7; 356/600

(58) Field of Classification Search ............. 356/237.1, 356/237.2, 237.3, 237.4, 237.5, 237.6, 239.1, 356/239.7, 446, 600
See application file for complete search history.

(56) References Cited

U.S. PATENT DOCUMENTS

| | | | | |
|---|---|---|---|---|
| 5,659,390 A | * | 8/1997 | Danko ..................... | 356/237.4 |
| 5,986,781 A | * | 11/1999 | Long ........................ | 359/30 |
| 6,201,601 B1 | * | 3/2001 | Vaez-Iravani et al. ... | 356/237.4 |
| 6,538,730 B2 | * | 3/2003 | Vaez-Iravani et al. ... | 356/237.2 |
| 6,862,096 B2 | * | 3/2005 | Vaez-Iravani et al. ... | 356/243.4 |
| 6,956,644 B2 | * | 10/2005 | Biellak et al. ........... | 356/237.4 |
| 7,002,677 B2 | * | 2/2006 | Bevis et al. ............. | 356/237.5 |

* cited by examiner

*Primary Examiner*—Gregory J. Toatley, Jr.
*Assistant Examiner*—Patrick Connolly
(74) *Attorney, Agent, or Firm*—Joshua D. Isenberg; JDI Patent (57) ABSTRACT

Spatial filtering is disclosed that improves the signal to noise ration of a sample inspection system of the type having a detector and collection optics that receive radiation scattered from a point on a sample surface and direct the scattered radiation toward the detector. The spatial filtering may screen the detector from substantially all of the forward-scattered radiation from back-scattered radiation that is scattered in a at an elevation angle less than about 45° with respect to a normal to the surface. Forward scattered noise is screened from the detector while backscattered signal reaches the detector. Programmable spatial filters may be used to selectively block scattered noise due to surface roughness while transmitting scattered signal due to surface defects.

39 Claims, 6 Drawing Sheets

SPATIAL FILTER FOR SAMPLE INSPECTION SYSTEM

FIELD OF THE INVENTION

This invention generally relates to optical sample inspection systems and more specifically to spatial filtering in optical sample inspection systems.

BACKGROUND OF THE INVENTION

Systems for inspecting semiconductor wafers or bare wafers have been proposed. See for example, U.S. Pat. No. 6,201,601. Systems such as those described in the above-referenced patent are useful for many applications, including the inspection of bare or unpatterned semiconductor wafers. Such systems typically scatter a laser beam from the wafer surface and collect the scattered radiation at a detector. The pattern of scattering can reveal defects in the wafer surface.

It is often desirable to use such sample inspection tools to inspect not only bare or unpatterned wafers but also rough surfaces, such as those found on the backside of a single-side polished (SSP) wafer. However, the extreme roughness of the surfaces involved often produces scattering noise that can be difficult to distinguish from signal scattered from defects. It is, therefore, desirable to provide an improved sample inspection system capable of distinguishing noise from defects on the backside of SSP wafers.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Sample Inspection Systems

According to embodiments of the present invention, spatial filtering can improve the signal to noise ration of a sample inspection system of the type having a detector and collection optics that receive radiation scattered from a point on a sample surface and direct the scattered radiation toward the detector. The spatial filtering screens the detector from substantially all of the forward-scattered radiation and from back-scattered radiation that is scattered in at an elevation angle less than about 45° with respect to a normal to the surface. Thus, forward scattered noise is screened from the detector while backscattered signal reaches the detector.

Figure 1:
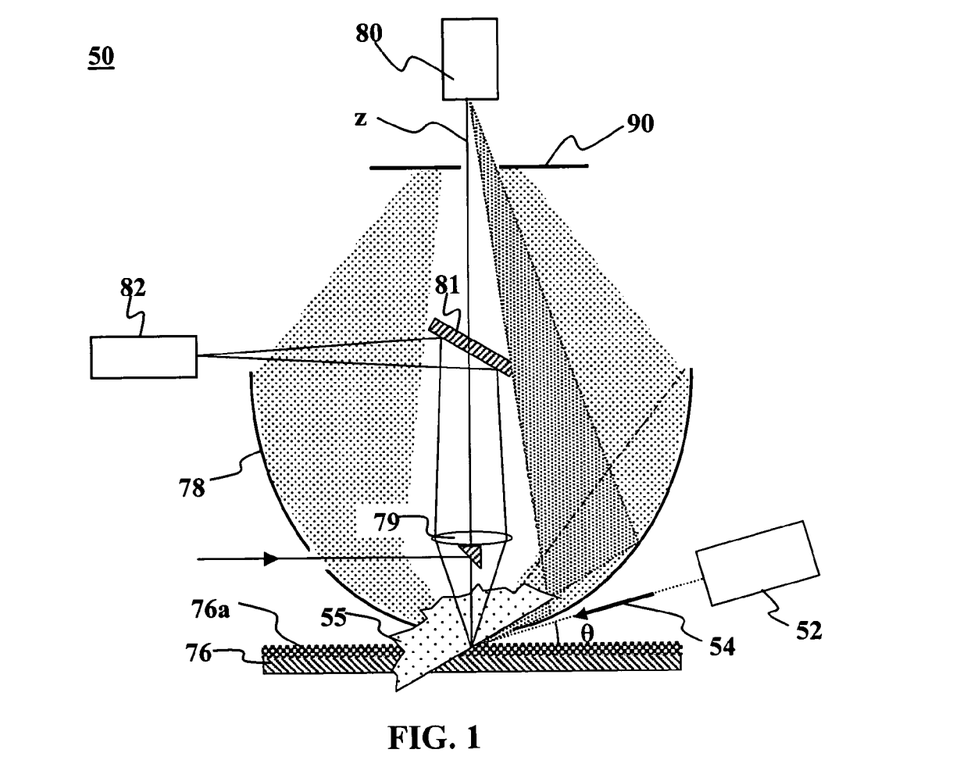
FIG. 1 is a vertical cross-section schematic diagram of a sample inspection system according to an embodiment of the present invention.

Embodiments of the present invention may be implemented in an optical sample inspection system. Such systems may be implemented in a number of ways. An example of such a system is described, e.g., in U.S. Pat. No. 6,201,601, the disclosures of which are incorporated herein by reference. An example of a system of this type is the SP1 Backside Inspection Module (BSIM) from KLA Tencor of Milpitas, Calif. By way of example FIG. 1 is a schematic view of a sample inspection system to illustrate a general set up for a sample inspection system 50 that may be used with embodiments of the present invention. In the system 50, a radiation source 52 may provide incident radiation 54 at one or more wavelengths in a wide electromagnetic spectrum (including but not limited to ultraviolet, visible, infrared). The radiation source 52 may be a laser providing the incident radiation 54 in the form of a laser beam. The system 50 may include two separate radiation sources for normal and oblique illumination of a surface 76a of a sample 76. In the oblique mode, the incident radiation 54 is incident on the surface 76a at an elevation angle θ with respect to the plane of the surface 76a. In some embodiments, the incident angle θ is chosen to be a Brewster angle for the surface 76a so the reflections containing most of the noise may be substantially reduced when a polarized incident radiation 54, e.g., P-polarized, illuminates the surface 76a.

The incident radiation 54 scatters from the surface 76a and the resulting scattered radiation 55 is collected by collection optics, e.g., a curved reflecting surface 78, such as a parabaloidal or ellipsoidal mirror. Curved reflecting surfaces 78 having shapes other than ellipsoidal or paraboloidal shapes may also be used. Preferably, each of such curved reflecting surfaces has symmetry axis z that is substantially coaxial with a normal to the surface 76a at a point where the incident radiation 54 strikes the surface 76a. The symmetry axis z defines an input aperture for receiving scattered radiation 55. There are many other possible configurations for the radiation source, and collections optics. All such variations are within the scope of the invention. The curved reflecting surface 78 directs the scattered radiation 55 to a detector 80, such as a photomultiplier tube. The signal from the detector 80 may be used to generate an image of defects on the surface 76a.

The collection optics may also include a lens 79 and mirror 81 to collect radiation scattered at low angles relative to the symmetry axis z and direct it to a second detector 82. A prism 83 may be located between the lens 79 and the sample to direct incident radiation onto the sample at or near normal incidence, e.g., along the symmetry axis z.

A spatial filter 90 is located between the collecting optics and the detector. The spatial filter 90 includes one or more portions that are opaque to the scattered radiation. The radiation forward scattered from a rough surfaces mostly contains noise while the backscattered radiation includes both signal and noise. However, in many cases, the noise tends to backscatter from rough surfaces a relatively low angles (e.g., less than about 45° with respect to the normal) and the signal tends to backscatter at relatively higher angles (e.g., greater than about 45°). Thus, to improve the ratio of signal to noise at the detector, the opaque portions of the spatial filter 90 may be configured to block part of the scattered radiation 55 that is primarily forward scattered and allow at least part of the scattered radiation 55 that is primarily backscattered to reach the detector 80. Note that in the embodiment depicted in FIG. 1, the mirror 79 may block some of the low-angle backscattered radiation. It is often the case (though not necessarily the case) that the collection optics cannot collect scattered radiation above some angle with respect to the normal. However, in other cases it may be desirable to optionally configure the spatial filter 90 to block backscattered radiation at elevation angles above some upper limit, e.g., about 75°

Thus forward scattered radiation and low-angle backscattered radiation may be blocked by appropriate configuration of the opaque and transmitting portions of the spatial filter 90. Appropriate configuration includes, but is not limited to, the size and/or shape of the opaque and transmitting portions of the spatial filter 90, the distance of the spatial filter from the surface 76a and the orientation of the spatial filter, e.g., relative top to the symmetry axis z.

Analytical Considerations

A sample inspection system of the type depicted in FIG. 1 can have a very large collection angle in dark field. A large collection angle makes such a system very sensitive for smooth wafers, such as prime silicon wafers. However, this large collection angle becomes a weakness when scanning a rough surface, such as the backside of a single side polished (SSP) wafer or other rough surface. The signal to noise ratio (SNR) for a sample inspection system determines its sensitivity. However, because of the heavy noise of a rough surface, suppressing the noise becomes the key factor for gaining a better sensitivity. Generally, one enhances SNR by increasing the signal and/or suppressing noise.

The scattered radiation 55 is scattered in a direction having an azimuthal component and elevation component with respect to the symmetry axis z. The inventor has analyzed the scatter distribution for both signal and noise from rough surfaces (e.g., the backside of SSP wafers). The analysis shows that for very rough wafers, i.e., wafers with surface features characterized by a relatively high spatial frequency compared to the frequency of incident radiation, most of the noise (i.e., radiation scattered from other surface features) is forward scattered, while most of the signal from small defects (i.e., radiation scattered from small defects), which actually determines the system sensitivity, is backscattered. Note that for very small defects, e.g., less than about 80 nm, most of the scattered radiation 55 is backscattered. An example of a worst-case noise distribution in the vertical plane is indicated schematically at 55 in FIG. 1. Nearly all of the backscattered noise is backscattered at angles less than about 45° with respect to the surface normal (symmetry axis z). Backscattered noise can be a significant problem if the noise is above a threshold of the detector 80. Based on the surface scatter distribution in 3-D, the inventor has developed a new spatial filter. This type of filter has been tested on backside inspection module (BSIM) systems with many different types of SSP wafers from different venders. The test results indicate that the new spatial filter significantly enhances BSIM sensitivity.

Figure 2A:
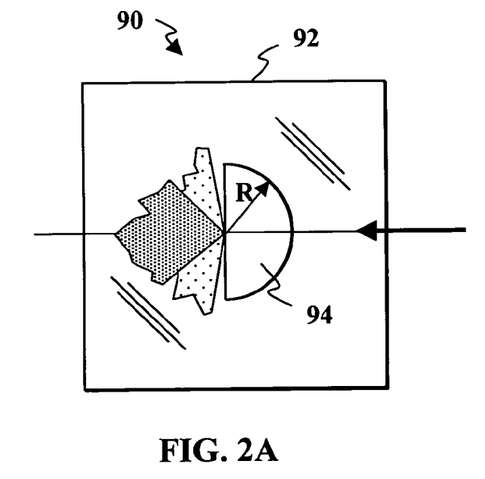
FIG. 2A is a plan view diagram of a spatial filter according to an embodiment of the present invention.
Figure 2B:
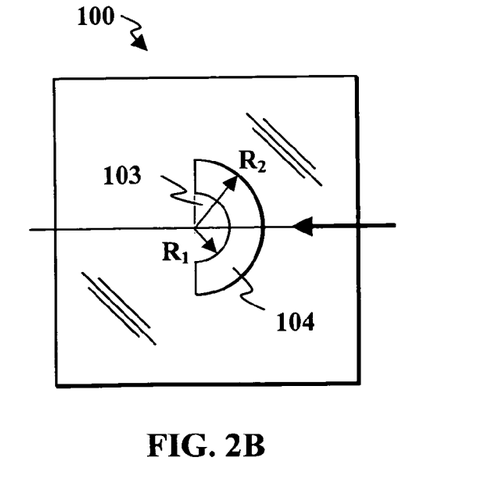
FIG. 2B is a plan view diagram of an alternative spatial filter according to an embodiment of the present invention.

FIG. 2A depicts an example of a design for the spatial filter 90 having an opaque portion and an opening. Examples low and high spatial frequency noise distributions in the plane of the sample are respectively indicated schematically as L and H in FIG. 2A. The direction of the incident radiation is shown by the arrow. To block forward scattered radiation, the spatial filter includes an opaque portion 92. To transmit high angle backscattered radiation, the spatial filter has an opening 94 in the shape of single wedge. By way of example, the opening 94 may be in the shape of a semicircle (i.e., 180° wedge angle) of radius R having a curved side that that faces the direction from which the incident radiation arrives. Alternatively, the opening 94 may a wedge angle smaller than 180°. The radius R of the semicircle and the height of the spatial filter above the sample surface determines a lower end of the range of elevation angles for which the spatial filter 90 transmits scattered radiation. Note that in the embodiment depicted in FIG. 1, some of the low-angle scattered radiation is blocked by the mirror 79. For surface inspection systems that lack such a feature, an alternative spatial filter 100 may also include an opening 104 with a semicircular opaque portion 103 that blocks the undesired low angle backscattered radiation, e.g., as shown in FIG. 2B. For a fixed height of the spatial filter 100 above the sample surface, the upper and lower ends of the desired range of elevation angles that can be transmitted may respectively be adjusted by appropriate choice of the radius $R_1$ of the opaque portion 103, the radius $R_2$ of the opening 103 and the distance between the spatial filter 100 and the scattering surface 76a. The spatial filter 94 may optionally include slots, notches, or other secondary openings in order to transmit selected portions of the forward scattered radiation or the low-angle backscattered radiation.

Figure 2C:
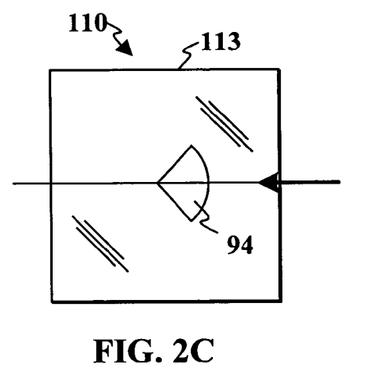
FIG. 2C is a plan view diagram of another alternative spatial filter according to an embodiment of the present invention.
Figure 2D:
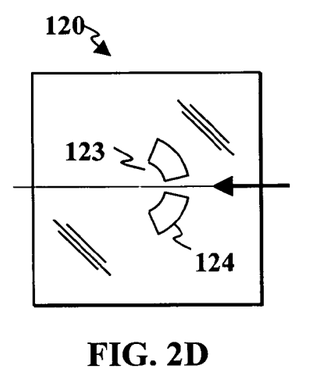
FIG. 2D is a plan view diagram of yet another alternative spatial filter according to an embodiment of the present invention.

Other configurations for the spatial filter 100 may reduce noise while enhancing the collection of signal. For example, FIG. 2C depicts a spatial filter 110 having an opaque portion 113 and a wedge shaped opening 114 with a wedge angle smaller than 180°. Furthermore, FIG. 2D depicts a spatial filter 120 having more two or more separate openings 124 in an opaque portion 123. Furthermore, although the opaque portions of the spatial filters shown in FIGS. 2A–2D are depicted as being substantially flat, the spatial filters may be made from opaque materials having curved surfaces.

Figure 3A:
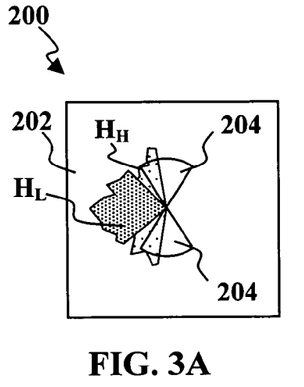
FIG. 3A depicts scattering diagrams for different spatial frequencies superimposed over a plan view of a spatial filter according to the prior art.
Figure 4A:
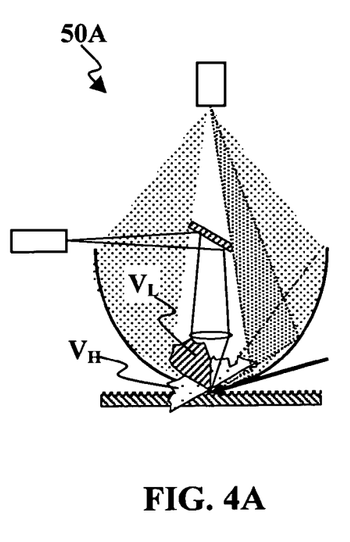
FIG. 4A is a is a vertical cross-section illustrating a sample inspection system with spatial filtering according to the prior art.

The advantages of the spatial filter described above may be seen when compared with prior art spatial filters. FIG. 3A depicts horizontal scattering diagrams $H_L$, $H_H$ for low spatial frequency and high spatial frequency noise superposed over a spatial filter 200 of the prior art. FIG. 4A depicts vertical scattering diagrams for $V_L$, $V_H$ for low and high spatial frequency noise superposed over a sample inspection system 50A of the type described above using the spatial filter 200 of the prior art. The prior art spatial filter 200 includes an opaque panel 202 with two wedge-shaped openings 204 arranged symmetrically with respect to the direction of incident radiation indicated by the arrow. The opaque panel 202 blocks both forward scattered and backscattered radiation while the openings transmit radiation scattered in the directions defined by their wedge shapes. Note that although the prior art filter 200 does block the noise in the low spatial frequency distributions $H_L$, $V_L$, it suffers two drawbacks for the high spatial frequency scattering distributions $H_H$, $V_H$. Specifically, for the high spatial frequency scattering distribution, the prior art spatial filter 200 transmits some of the forward scattered noise. Which raises the overall noise level at the detector. Furthermore, the prior art spatial filter blocks a significant portion of backscattered signal as well as backscattered noise. This lowers the overall signal at the detector. Both of these effects tend to decrease the SNR.

Figure 3B:
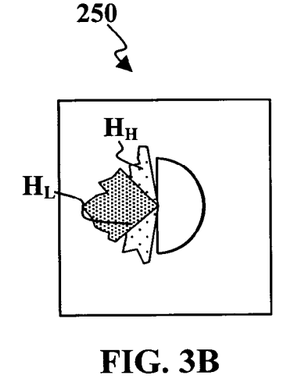
FIG. 3B depicts scattering diagrams for different spatial frequencies superimposed over a plan view diagram of a spatial filter according to an embodiment of the present invention.
Figure 4B:
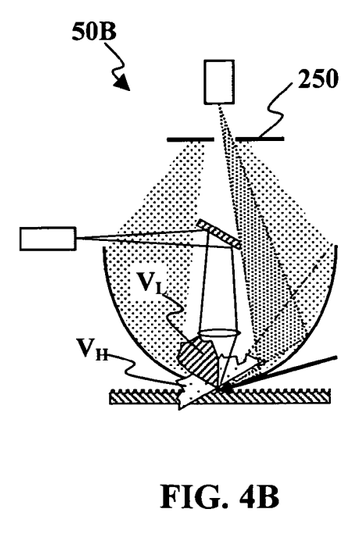
FIG. 4B is a vertical cross-section illustrating a sample inspection system with spatial filtering according to an embodiment of the present invention.

FIG. 3B depicts scattering diagrams for low spatial frequency and high spatial frequency noise superposed over a spatial filter 250 of the type shown in FIG. 2A. FIG. 4B depicts scattering diagrams for high spatial frequency noise superposed over a sample inspection system 50B of the type described above, using spatial filtering according to embodiments of the present invention. Note that the spatial filtering 250 blocks all of the forward scattered high spatial frequency noise and transmits the backscattered high spatial frequency signal. Backscattered noise at low elevation angles (e.g., below about 45° with respect to the normal) can be blocked either by spatial filter or other parts of the inspection system 50B. These effects lead to a greater SNR compared to the prior art system 50A.

Figure 5A:
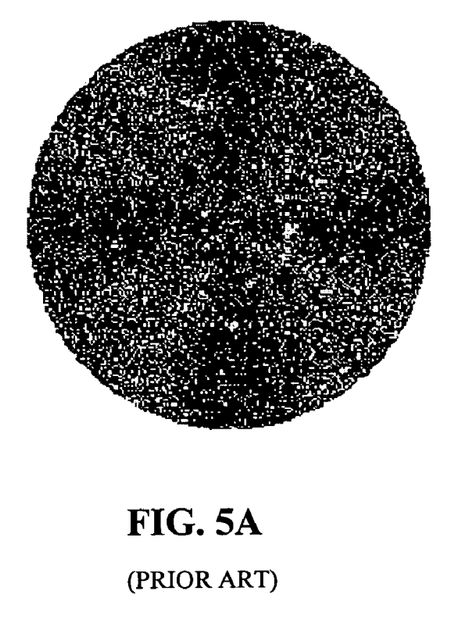
FIG. 5A is a haze map taken from a single side polished mirror using a sample inspection system of the type depicted in FIG. 1 with spatial filtering according to the prior art.
Figure 5B:
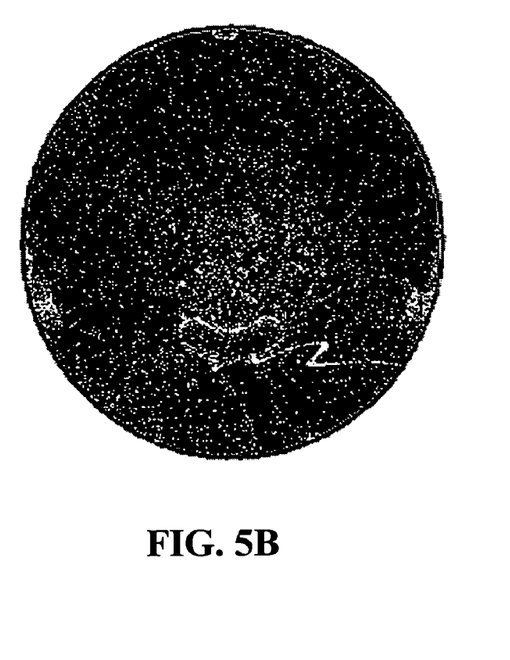
FIG. 5B is a haze map taken from a single side polished mirror using a sample inspection system of the type depicted in FIG. 1 with spatial filtering according to an embodiment of the present invention.

As an example of the improved performance that is possible with the spatial filter of the present invention, experiments have been performed comparing prior art type spatial filters to spatial filters according to embodiments of the present invention. The haze maps of FIGS. 5A–5B illustrate the results of these experiments. Specifically, FIG. 5A depicts a haze map for an area of defects in a Wacker SSP Wafer from Advanced Micro Devices taken using a KLA Tencor SP1 BSIM using a spatial filter of the type depicted in FIG. 3A with twin 40° wedges. FIG. 5B depicts a haze map for the same area of the same wafer taken using the same SP1 BSIM using a spatial filter of the type depicted in FIG. 2A. The defect features appear much more prominently in FIG. 5B than in FIG. 5A. The SP1 haze map gives "Raw Data" (data without threshold), and is generated from Rppm mode. Such haze maps can be used as an indicator to show how much noise is detected/collected by SP1. By comparing the haze maps with and without spatial filtering according to embodiments of the present invention, it is clear that embodiments of the present invention successfully block the diffraction noise from SSP wafers.

ALTERNATAIVE EMBODIMENTS

Figure 6A:
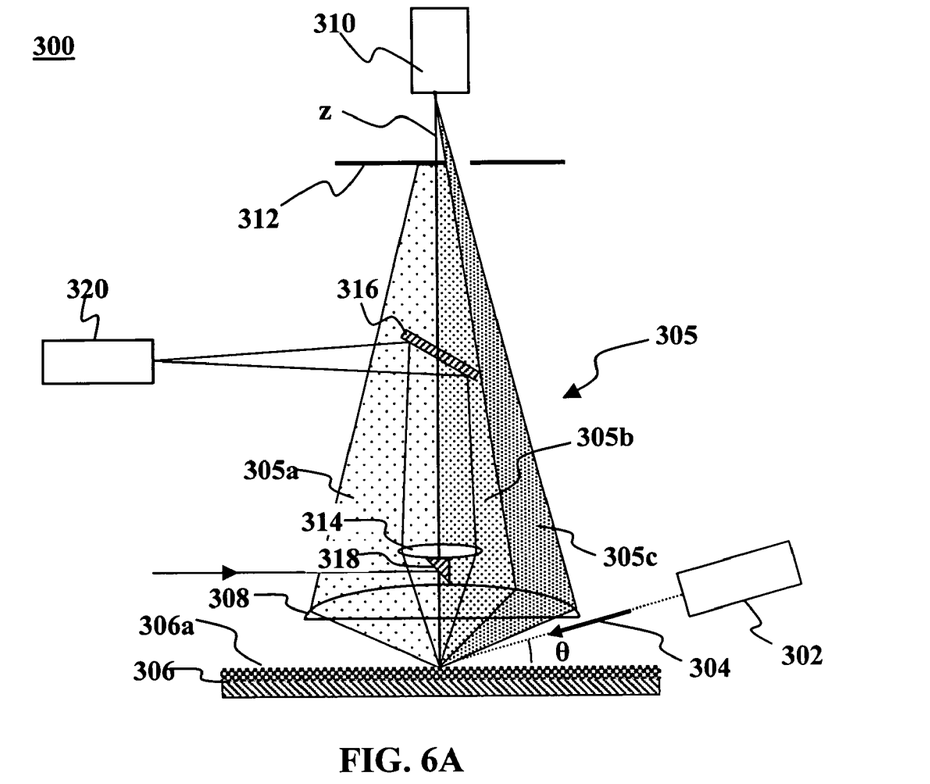
FIG. 6A is a vertical cross-section schematic diagram of a sample inspection system using refractive collecting optics according to an embodiment of the present invention.

In the examples discussed above, the spatial filters have been configured for use with sample inspection systems that use reflective collecting optics. In alternative embodiments, a sample inspection system may use refractive collecting optics. Such a collecting system may utilize a spatial filter having a different configuration than those shown above. For example, FIG. 6A depicts a sample inspection system 300 that may be used with embodiments of the present invention. In the system 300, a radiation source 302 may provide incident radiation 304 at one or more wavelengths as described above. The system 300 may include radiation sources for normal and oblique illumination of a surface 306a of a sample 306. In the oblique mode, the incident radiation 304 is incident on the surface 306a at an elevation angle θ, which may be a Brewster angle as described above.

The incident radiation 304 scatters from the surface 306a and the resulting scattered radiation 305 is collected by refractive collection optics 308, e.g., one or more lenses, and directed towards a detector 310. The collection optics may be symmetric about an axis z that is substantially coaxial with a normal to the surface 306a at a point where the incident radiation 54 strikes the surface 306a. The scattered radiation 305 includes forward scattered radiation 305a, low-angle backscattered radiation 305b and high-angle backscattered radiation 305c. A spatial filter 312 is located along an optical path between the sample surface 306a and the detector 310. The spatial filter 312 includes one or more opaque portions that block the forward scattered radiation (or selected portions thereof) and/or the low-angle backscattered radiation (or selected portions thereof).

Figure 6B:
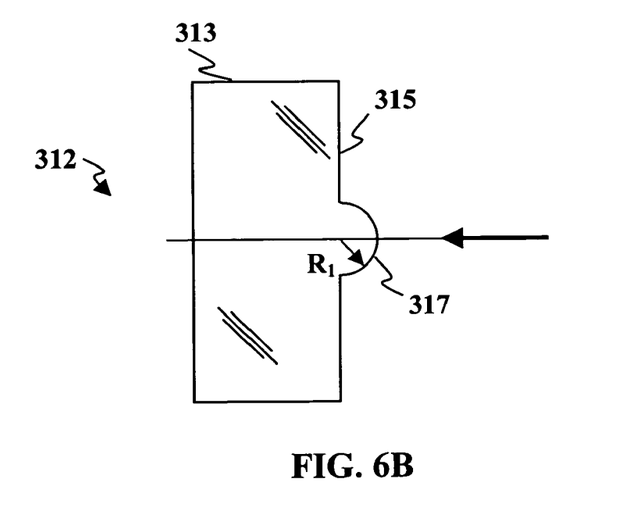
FIG. 6B is a plan view diagram of a spatial filter for use with the sample inspection system of FIG. 6A.

The spatial filter 312 may have a substantially planar shape and may be oriented in a plane substantially parallel to the surface 306a. Alternatively, the spatial filter 312 may be made from opaque materials having curved surfaces. By way of example, FIG. 6B depicts one possible layout, among others, for the spatial filter 312. As shown in FIG. 6B, the spatial filter 312 may include a first opaque 313 portion that blocks the forward scattered radiation. The first opaque portion may be a substantially rectangular section having an edge 315. The edge 315 may lie along a line that is substantially perpendicular to the direction of the incident radiation 304 as indicated by the arrow. The edge 315 may intersect the symmetry axis z. The spatial filter 312 may include a second opaque portion 317 that blocks the low angle forward scattered radiation. In the example shown in FIG. 6B, the second opaque portion 317 may have an arcuate (e.g., semicircular) shape and may protrude from the edge 315 of the first opaque portion 313. The second opaque portion 317 may be centered on the symmetry axis z and may be characterized by a radius R. The value of R and the distance from the spatial filter 312 to the surface 306a determine the maximum elevation angle for radiation blocked by the spatial filter. The first and second portions 313, 317 may include slots, notches, or other openings in order to transmit selected portions of the forward scattered radiation or the low-angle backscattered radiation.

The system 300 may also include a lens 314 and mirror 316 to collect radiation scattered at low angles relative to the symmetry axis z and direct it to a second detector 320. In addition, a prism 318 may be located between the lens 314 and the sample 306 to direct incident radiation onto the sample at near normal incidence, e.g., along the symmetry axis z. These elements of the system may act to block some of the scattered radiation 305. In addition, the collection optics 308 may have a finite aperture that places an upper limit on the range of elevation angle of the scattered radiation 305 that is collected. Thus, these components of the system 300 may act as part of the spatial filter 312.

Figure 7A:
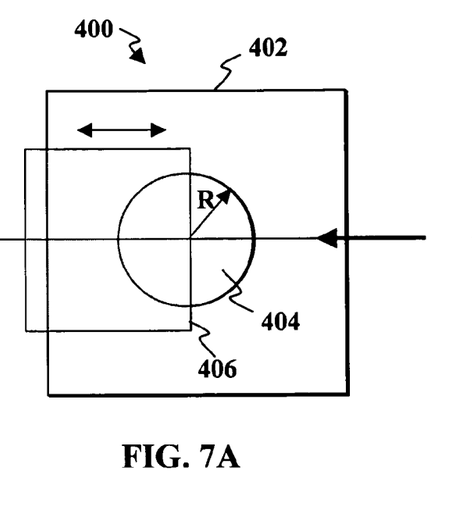
FIG. 7A is a plan view diagram of a variable spatial filter according to an embodiment of the present invention.
Figure 7B:
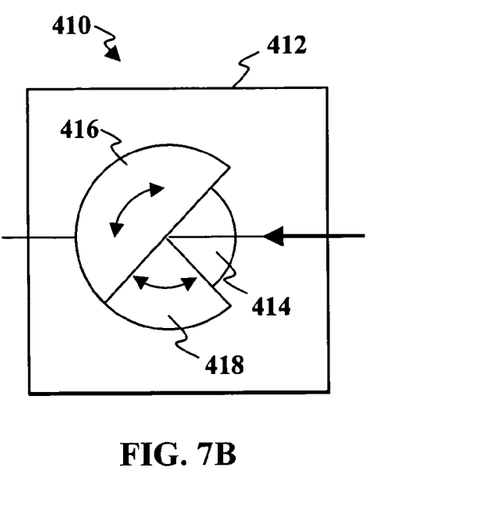
FIG. 7B is a plan view diagram of an alternative variable spatial filter according to an embodiment of the present invention.

By way of example, spatial filters of the types described above may be made from solid material, e.g., metal, by standard stamping, etching, masking, deposition and other techniques. Such techniques may produce spatial filters having openings of a fixed shape and size. It is also possible for the spatial filter to having an opening characterized by an adjustable shape and size. The size and shape of the opening may be adjusted mechanically, e.g., by covering the opening with a movable vane. For example, FIG. 7A depicts a spatial filter 400 having an opaque portion 403 with a circular opening 404 and a rectangular vane 406 that can move as shown by the arrow. The vane 406 translates to selectively block part of the opening 404. Alternatively, as shown in FIG. 6B, a spatial filter 410 may have an opaque portion 413 with a circular opening 414 and two vanes 416, 418 that rotate about a common pivot point to cover portions of the opening 414. Those of skill in the art will be able to devise many different configurations of moveable vanes and openings, e.g., by varying the size, shape and number of openings or vanes or by combining translating and rotating vanes or by vanes that both rotate and translate.

Alternatively, the spatial filter may include a variable optical material having optical properties that may change under external influence such as electric or magnetic fields, temperature, or radiation. The variable optical material may be divided into a plurality of sections, each section being selectively configurable to be either substantially opaque or substantially radiation-transmitting. Examples of such variable optical materials include liquid crystals. Liquid crystals possess less geometrical regularity or order than normal solid crystals. The order of a liquid crystal may vary in response to alterations in temperature and other quantities such as an applied electric field. Liquid crystals are characterized by phase varieties, including cholesteric, nematic and smectic.

Figure 8A:
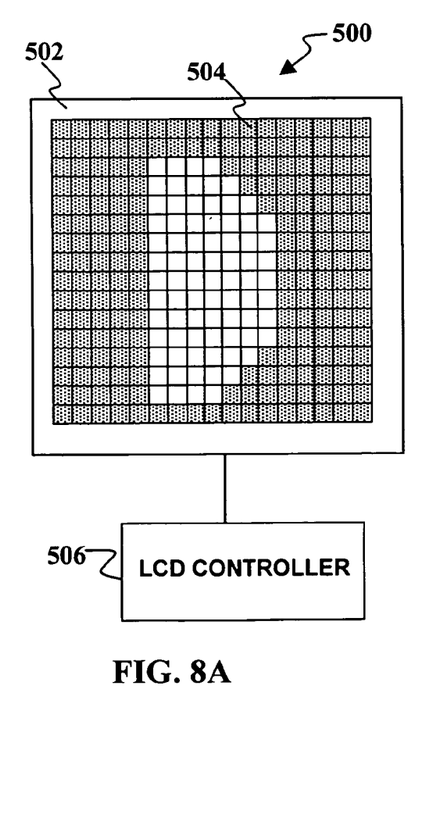
FIG. 8A is a plan view schematic diagram of a programmable spatial filter according to an embodiment of the present invention.

By way of example, FIG. 8A depicts an example of a programmable spatial filter 500, which may be made from a liquid crystal display (LCD) panel 502 divided up into sections or pixels 504. Each pixel may include, e.g., a liquid crystal layer and a polarizer disposed between two transparent electrodes. When a voltage is applied across the electrodes the liquid crystal layer becomes polarized. By appropriate orientation of the polarizer, the pixels 504 may change from a light transmitting state to a substantially opaque state under the control of electrical signals from a controller 506. By way of example, the LCD panel 502 may be of a commercial type commonly used in conjunction with an overhead projector for projecting images from a computer display onto a screen. By way of example, and without loss of generality, the controller 506 may be a commercially available LCD A/D controller, e.g. a model TC10001L or model TC10002L controller available from Panel-Solutions Group (http://www.panel-solutions.com). Alternatively, the controller 506 may be a general-purpose computer running software that provides an image of the desired spatial filter pattern to the LCD panel 502. The software may be a common graphics or imaging software or an application-specific program that changes the pattern of the spatial filter 500 in response to a measured pattern of signal and noise.

Figure 8B:
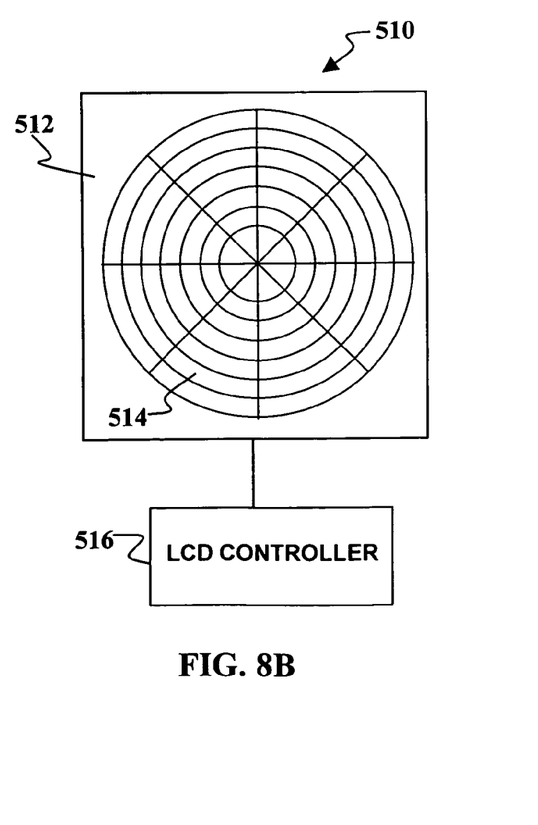
FIG. 8B is a plan view schematic diagram of an alternative programmable spatial filter according to an embodiment of the present invention.

It is important that, in the transmitting state, the pixels 504 are substantially transparent (or at least translucent) to radiation in the wavelengths range of the scattered radiation. For example, where the incident radiation is in the ultraviolet range, the pixels should be transparent to the ultraviolet when they are in the transmitting state. The pixels 504 may be arranged in a rectangular grid pattern, as shown in FIG. 8A. Commercially available liquid crystal displays are often made with such a pixel pattern. Such displays often have a pixel density of several hundred pixels per inch and can be several inches across. However, other pixel patterns may be more appropriate for certain spatial filter geometries. For example, FIG. 8B depicts a programmable spatial filter 510 which may be made from a liquid crystal display (LCD) panel 512 divided up into sections or pixels 514 in the shape of concentric wedges and/or arcuate segments. By appropriate signals from the controller 514, the pixels may be turned on or off to produce spatial filter patterns of the types depicted above among others.

Figure 9:
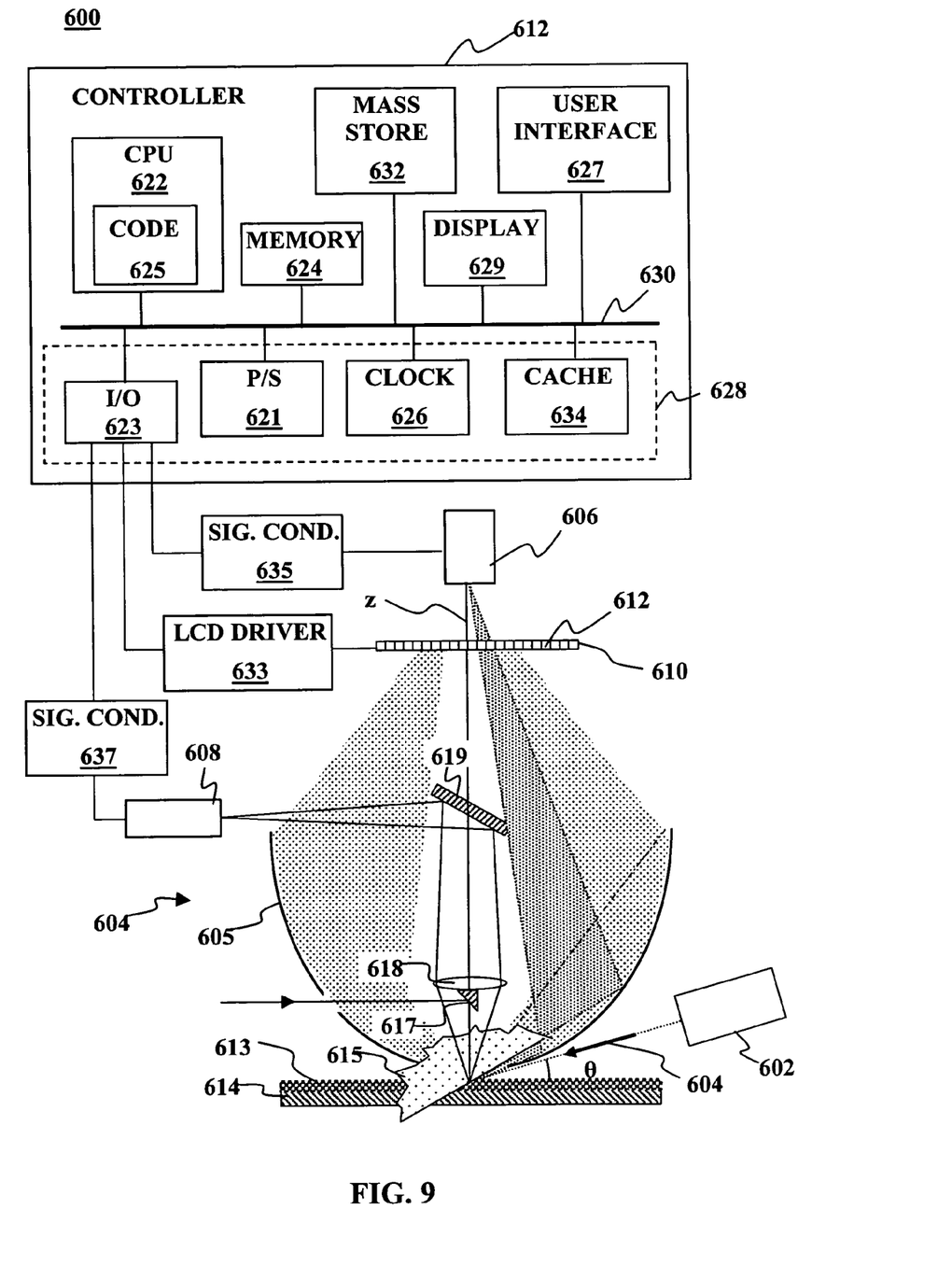
FIG. 9 is a vertical cross-section schematic diagram of a sample inspection system according to an alternative embodiment of the present invention.

Due to the great flexibility, a given programmable spatial filter may be used in different sample inspection systems. Furthermore, programmable spatial filters may be adjusted in real time during operation of the system in order to optimize signal to noise performance. A programmable spatial filter of the type described above with respect to FIG. 8A or FIG. 8B may be incorporated into a sample inspection system according to another embodiment of the present invention. FIG. 9 depicts an example of such a sample inspection system 600 wherein a programmable spatial filter can be adjusted in real time in response to a measured pattern of signal and noise. The system 600 includes a radiation source 602, collection optics 604, a detector 606, an optional imaging device 608, a programmable spatial filter 610, and a controller 620. The source 602 provides incident radiation 611 that impinges on a surface 613 of a sample 614. The collection optics 604 direct scattered radiation 615 from the surface 614 toward the detector 606 and the imaging device 608. The controller 620 adjusts a mask pattern of the spatial filter 610 in a way that increases signal relative to noise at the detector 606.

The radiation source 602 may be a laser or other source of radiation suitable for use in a sample inspection system, e.g., as described above. The collection optics may include some combination of reflecting or refractive optical components. By way of example, the collecting optics 604 may include a curved reflecting surface 616, one or more lenses 618 and one or more mirrors 619. The curved reflecting surface 616 may be symmetric about a symmetry axis z that is substantially perpendicular to the surface 613. The system may include a secondary source of radiation (not shown) that is directed to the surface 613 at or near normal incidence, e.g., by a mirror 617. Scattered secondary radiation may be collected by the imaging device 608 and converted to an image in which radiation scattered from surface defects is distinguishable from noise scattered due to general surface roughness.

The programmable spatial filter 610 may be, e.g., one of the types described above. In a particular example, the spatial filter 610 may be implemented using a LCD-type screen having pixels 612 that are selectively either transmitting or opaque.

In a particular embodiment, the optional imaging device 608 may produce an image of a pattern of scattered radiation having both signal and noise and send the image to the controller 620. The controller 620 analyzes the image, distinguishes the signal from the noise. By way of example, the imaging device 608 may be a charge coupled device (CCD) that converts received pattern of optical signals in to a pattern of electrical signals, e.g. with the strength of the electrical signal corresponding to the optical signal received from a given part of the surface 613. In some cases, noise from the general surface roughness appears as a more or less uniformly distributed signal, i.e., one that does not depend significantly on the location from which it is received. Signal from surface defects appears as localized places where the intensity differs significantly from the background noise. The controller 620 may analyze the image to determine the ratio of signal to noise and, e.g., by a simple feedback algorithm, adjust the pattern on the spatial filter 610 to optimize the ratio of signal to noise. Alternatively, the controller 620 may determine the location of the point of origin of scattered radiation corresponding to a given signal or noise, compute a range of solid angles for noise to block or signal to transmit and convert the solid angle information to a set of pixels 612 to make either transmitting or opaque.

Note that the imaging device 608 and mirror 619 (if any) may be located at any point suitable for collection of the scattered radiation 615. For example, the mirror 619 may be located between the surface 613 and the spatial filter 612 as shown in FIG. 9 to so that the imaging device 608 collects at least part of the scattered radiation before it reaches the spatial filter 612. Alternatively, the imaging device 608 may collect scattered radiation at some point between the spatial filter 612 and the detector 606. Furthermore, it is possible for the detector 606 and imaging device 608 to be one and the same. All such variations are within the scope of embodiments of the present invention.

The controller 620 may be a self-contained microcontroller. Alternatively, the controller 620 may be a general purpose computer configured to include a central processor unit (CPU) 622, memory 624 (e.g., RAM, DRAM, ROM, and the like) and well-known support circuits 628 such as power supplies 621, input/output (I/O) functions 623, clock 626, cache 634, and the like, coupled to a control system bus 630. The memory 624 may contain instructions that the CPU 622 executes to facilitate the performance of the system 600. The instructions in the memory 624 may be in the form of the program code 625. The code 625 may conform to any one of a number of different programming languages such as Assembly, C++, JAVA or a number of other languages. The controller 620 may also include an optional mass storage device, 632, e.g., CD-ROM hard disk and/or removable storage, flash memory, and the like, which may be coupled to the control system bus 630. The controller 620 may optionally include a user interface 627, such as a keyboard, mouse, or light pen, coupled to the CPU 622 to provide for the receipt of inputs from an operator (not shown). The controller 620 may also optionally include a display unit 629 to provide information to the operator in the form of graphical displays and/or alphanumeric characters under control of the processor unit 622. The display unit 629 may be, e.g., a cathode ray tube (CRT) or flat screen monitor.

The controller 620 may exchange signals with the imaging device 606, the detector 608 and the programmable spatial filter 610 through the I/O functions 623 in response to data and program code instructions stored and retrieved by the memory 624. Depending on the configuration or selection of controller 620 the imaging device 606, detector 608 and programmable spatial filter 610 may interface with the I/O functions via conditioning circuits, including, e.g., an LCD driver 633, signal conditioners 635, 637. The conditioning circuits may be implemented in hardware or software form, e.g., within code 625, such that I/O functions 623 may directly connect to each respective switch component.

Although the above embodiment of the invention is described herein as being implemented in software and executed upon a general purpose computer, those skilled in the art will realize that the invention could be implemented using hardware such as an application specific integrated circuit (ASIC), microcontroller or other hardware circuitry. As such, it should be understood that the invention may be implemented, in whole or in part, in software, hardware or both.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A sample inspection system, comprising:
   collection optics that receive radiation scattered from a point on a sample surface proximate a symmetry axis of said collection optics and originating from an incident radiation directed at an oblique angle with respect to said sample surface, said collection optics being further configured to direct the scattered radiation to a detector
   a spatial filter disposed between said collection optics and the detector,
   said spatial filter being configured to screen the detector from substantially all of the scattered radiation that is scattered in a direction having a forward azimuthal component relative to the incident radiation,
   said spatial filter or system being configured to screen the detector from the scattered radiation scattered in a direction having a backward azimuthal component relative to the incident radiation and an elevation angle less than about 45° with respect to a normal to the surface
   whereby the detector is screened from forward scattered noise while a backscattered signal is allowed to reach the detector.

2. The system of claim 1 wherein said spatial filter includes an opaque material having an opening in the shape of a single wedge.

3. The system of claim 2 wherein said wedge has a symmetry axis aligned with a direction of incidence of said incident radiation.

4. The system of claim 2 wherein said wedge is substantially semicircular.

5. The system of claim 1 wherein the spatial filter transmits to the detector the scattered radiation that is scattered in a direction having a backward azimuthal component relative to the incident radiation and an elevation angle greater than about 45° with respect to a normal to the sample surface.

6. The system of claim 1 wherein said collection optics collects said scattered radiation scattered at elevation angles between about 25° and about 75° with respect to said normal and directs the collected scattered radiation toward the detector.

7. The system of claim 1 wherein said spatial filter and/or system is configured to screen the detector from said scattered radiation scattered in a direction having a backward azimuthal component relative to said incident radiation and an elevation angle less than about 45° with respect to a normal to said surface.

8. The system of claim 7 wherein the spatial filter transmits to the detector the scattered radiation that is scattered in a direction having a backward azimuthal component relative to the incident radiation and an elevation angle greater than about 55° with respect to a normal to the sample surface.

9. The system of claim 1 wherein said spatial filter includes an opaque portion that blocks undesired backscattered radiation.

10. The system of claim 1 wherein the spatial filter includes an opaque portion.

11. The system of claim 10 wherein the opaque portion is adjustable.

12. The system of claim 10 wherein the opaque portion includes an opening.

13. The system of claim 12 opening is adjustable.

14. The system of claim 1 wherein the distance between the spatial filter and the sample surface is adjustable.

15. The system of claim 1 wherein said spatial filter includes a variable optical material having a plurality of pixels, each pixel being selectively configurable in either a first state or a second state, the pixel being substantially opaque in the first state and substantially radiation-transmitting in the second state.

16. The system of claim 15, further comprising a controller coupled to the spatial filter.

17. The system of claim 16, further comprising an imaging device coupled to the controller.

18. The system of claim 17 wherein the imaging device receives radiation scattered from the sample surface.

19. The system of claim 18 wherein the imaging device produces an image wherein a signal from defects on the surface is distinguishable from a background noise due to surface roughness.

20. A spatial filter for a sample inspection system of the type having collection optics including a curved mirrored surface that receives radiation scattered from a point on a sample surface proximate a symmetry axis of the curved reflecting surface and direct the scattered radiation toward a detector, said spatial filter comprising:
an opaque portion;
said opaque portion being configured such that when the spatial filter is disposed between the collection optics and the detector, said opaque portion screens the detector from substantially all of the scattered radiation that is scattered in a direction having a forward azimuthal component relative to an incident radiation,
said portion being sized and shaped such that when the spatial filter is disposed between the collection optics and the detector the opaque portion screens the detector from the scattered radiation scattered in a direction having a backward azimuthal component relative to the incident radiation and an elevation angle less than about 45° with respect to a normal to the sample surface,
whereby said opaque portion screens the detector from forward scattered noise while the opening allows a backscattered signal to reach the detector.

21. The spatial filter of claim 20 wherein the opaque portion includes an opening.

22. The spatial filter of claim 21 wherein the opening is in the shape of a single wedge.

23. The spatial filter of claim 22 wherein said wedge has a symmetry axis aligned with a direction of incidence of said incident radiation.

24. The spatial filter of claim 23 wherein said wedge is substantially semicircular.

25. The spatial filter of claim 21 wherein the opaque portion and opening are configured such that when the spatial filter is disposed between the collection optics and the detector the opaque portion screens the detector from said scattered radiation scattered in a direction having a backward azimuthal component relative to said incident radiation and an elevation angle less than about 45° with respect to a normal to said surface.

26. The spatial filter of claim 21 wherein the opening is sized and shaped said opening being sized and shaped such that when the spatial filter is disposed between the collection optics and the detector the opening transmits to the detector the scattered radiation that is scattered in a direction having a backward azimuthal component relative to the incident radiation and an elevation angle greater than about 45° with respect to a normal to the sample surface.

27. The spatial filter of claim 21 wherein the opening is sized and shaped said opening being sized and shaped such that when the spatial filter is disposed between the collection optics and the detector the opening transmits to the detector the scattered radiation that is scattered in a direction having a backward azimuthal component relative to the incident radiation and an elevation angle greater than about 55° with respect to a normal to the sample surface.

28. The spatial filter of claim 21 wherein the configuration of the opening and/or opaque portion is adjustable.

29. The spatial filter of claim 20 wherein the configuration of the opaque portion is adjustable.

30. The spatial filter of claim 20 wherein the spatial filter includes a variable optical material having a plurality of pixels, each pixel being selectively configurable in either a first state or a second state, the pixel being substantially opaque in the first state and substantially radiation-transmitting in the second state.

31. The spatial filter of claim 30 further comprising a controller coupled to the plurality of pixels, the controller being configured to provide one or more signals that determine whether a given pixel is in the first state or the second state.

32. In a sample inspection system of the type having collection optics including a collection optics that receive radiation scattered from a point on a sample surface proximate a symmetry axis of the collection optics and direct the scattered radiation toward a detector, a method for enhancing a signal to noise ratio, the method comprising the steps of:
screening the detector from substantially all of the scattered radiation that is scattered in a direction having a forward azimuthal component relative to an incident radiation; and
screening the detector from the scattered radiation that is scattered in a direction having a backward azimuthal component relative to an incident radiation and an elevation angle less than about 45° with respect to a normal to the surface,
whereby forward scattered noise is screened from the detector while backscattered signal reaches the detector.

33. The method of claim 32 further comprising transmitting to the detector the scattered radiation that is scattered in a direction having a backward azimuthal component relative to the incident radiation and an elevation angle greater than about 45° with respect to a normal to the sample surface.

34. The method of claim 32 further comprising transmitting to the detector the scattered radiation that is scattered in a direction having a backward azimuthal component relative to the incident radiation and an elevation angle greater than about 55° with respect to a normal to the sample surface.

35. The method of claim 32 wherein the incident radiation is incident on the surface at a Brewster angle with respect to the surface.

36. In a sample inspection system of the type having collection optics including a collection optics that receive radiation scattered from a point on a sample surface proximate a symmetry axis of the collection optics and direct the scattered radiation toward a detector, a method for enhancing a signal to noise ratio, the method comprising the steps of:

collecting part of the scattered radiation with an imaging device;

generating an image of the scattered radiation wherein a signal from defects on the surface is distinguishable from a background noise due to surface roughness; and in response to the image, selectively screening the detector from portions of the scattered radiation corresponding to the background noise.

37. The method of claim 36 wherein selectively screening the detector includes the use of a programmable spatial filter including a variable optical material having a plurality of pixels, each pixel being selectively configurable in either a first state or a second state, the pixel being substantially opaque in the first state and substantially radiation-transmitting in the second state.

38. The method of claim 37 wherein the variable optical material is a liquid crystal display panel.

39. The method of claim 36 wherein selectively screening the detector from portions of the scattered radiation corresponding to the background noise includes:

screening the detector from substantially all of the scattered radiation that is scattered in a direction having a forward azimuthal component relative to an incident radiation; and screening the detector from the scattered radiation that is scattered in a direction having a backward azimuthal component relative to an incident radiation and an elevation angle less than about 45° with respect to a normal to the surface, whereby forward scattered noise is screened from the detector while backscattered signal reaches the detector.

* * * * *